United States Patent
Rathjen

(10) Patent No.: US 11,944,576 B2
(45) Date of Patent: *Apr. 2, 2024

(54) OPHTHALMOLOGICAL APPARATUS FOR TREATING EYE TISSUE USING A PULSED LASER BEAM

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 449 days.

This patent is subject to a terminal disclaimer.

(21) Appl. No.: 17/363,493

(22) Filed: Jun. 30, 2021

(65) Prior Publication Data

US 2021/0322215 A1   Oct. 21, 2021

Related U.S. Application Data

(63) Continuation of application No. 16/224,945, filed on Dec. 19, 2018, now Pat. No. 11,096,826.

(30) Foreign Application Priority Data

Dec. 20, 2017   (EP) ..................................... 17209073

(51) Int. Cl.
*A61F 9/008* (2006.01)

(52) U.S. Cl.
CPC ............ *A61F 9/0084* (2013.01); *A61F 9/008* (2013.01); *A61F 9/00804* (2013.01);
(Continued)

(58) Field of Classification Search
CPC .. A61F 9/008; A61F 9/00804; A61F 9/00814; A61F 9/00827; A61F 9/0084;
(Continued)

(56) References Cited

U.S. PATENT DOCUMENTS 6,325,792 B1 * 12/2001 Swinger .............. A61F 9/00834
606/4
7,530,692 B2   5/2009 Yamaguchi et al.
(Continued)

FOREIGN PATENT DOCUMENTS

EP   1731120 A1   12/2006
EP   2596775 A1   5/2013

OTHER PUBLICATIONS

Apr. 30, 2018—(EP) Search Report—U.S. Appl. No. 17/209,073.

*Primary Examiner* — Christopher A Flory
(74) *Attorney, Agent, or Firm* — Banner & Witcoff, Ltd.

(57) ABSTRACT

An ophthalmological apparatus comprises a laser source for producing a pulsed laser beam, a scanner system for deflecting the pulsed laser beam at a treatment speed in the eye tissue along a scanning treatment line, a first scanning apparatus connected upstream of the scanner system for deflecting the pulsed laser beam and for producing a first scanning movement component superposed on the scanning treatment line in a first scanning direction at a first scanning speed that is higher as compared to the treatment speed, and a second scanning apparatus connected upstream of the scanner system for deflecting the pulsed laser beam and for producing a second scanning movement component, which is superposed on the first scanning movement component in a second scanning direction, which is at an angle to the first scanning direction, at a second scanning speed that is higher as compared to the first scanning speed.

16 Claims, 3 Drawing Sheets

(52) U.S. Cl.
CPC ...... *A61F 9/00814* (2013.01); *A61F 9/00827* (2013.01); *A61F 2009/0087* (2013.01); *A61F 2009/00872* (2013.01); *A61F 2009/00874* (2013.01); *A61F 2009/00897* (2013.01)

(58) Field of Classification Search
CPC .... A61F 2009/0087; A61F 2009/00872; A61F 2009/00874; A61F 2009/00897
See application file for complete search history.

(56) References Cited

U.S. PATENT DOCUMENTS

| | | | |
|---|---|---|---|
| 7,621,637 B2 | 11/2009 | Rathjen et al. | |
| 9,737,436 B2 | 8/2017 | Rathjen et al. | |
| 2004/0243112 A1 | 12/2004 | Bendett et al. | |
| 2007/0252950 A1 | 11/2007 | Kraats et al. | |
| 2008/0212623 A1* | 9/2008 | Bischoff | B23K 26/0876 606/4 |
| 2011/0028958 A1 | 2/2011 | Raksi et al. | |
| 2011/0118712 A1* | 5/2011 | Lubatschowski | A61F 9/008 606/5 |
| 2011/0137299 A1* | 6/2011 | Donitzky | A61F 9/008 606/4 |
| 2012/0029491 A1 | 2/2012 | Rathjen | |
| 2013/0144277 A1 | 6/2013 | Rathjen et al. | |
| 2013/0150837 A1 | 6/2013 | Rathjen et al. | |
| 2013/0155375 A1 | 6/2013 | Rathjen et al. | |
| 2016/0235584 A1* | 8/2016 | Papastathopoulos | A61F 9/008 |
| 2017/0304114 A1 | 10/2017 | Rathjen et al. | |
| 2018/0125708 A1* | 5/2018 | Böhme | A61F 9/00825 |
| 2019/0110926 A1* | 4/2019 | Malek Tabrizi | A61F 9/00836 |

* cited by examiner

OPHTHALMOLOGICAL APPARATUS FOR TREATING EYE TISSUE USING A PULSED LASER BEAM

CROSS REFERENCE TO RELATED APPLICATIONS

This application is a continuation of U.S. application Ser. No. 16/224,945, filed Dec. 19, 2018, which claims benefit of European Patent Application No. 17209073.0, filed Dec. 20, 2017, the disclosure of which is herein incorporated by reference in its entirety.

TECHNICAL FIELD

The present disclosure relates to an ophthalmological apparatus for treating eye tissue using a pulsed laser beam, and in particular to an ophthalmological apparatus for tissue volume treatment in the eye tissue using a pulsed laser beam.

BACKGROUND

For treating eye tissue using a laser beam, a treatment region is scanned with laser pulses by guiding the pulsed laser beam along a scanning treatment line using suitable scanner systems (deflection apparatuses). Deflecting the light beams or laser pulses, for example femtosecond laser pulses, is generally effected by way of movable mirrors which are pivotable about one or two scan axes and deflect the pulsed laser beam into one or two scanning directions, for example using galvano scanners, piezo scanners, polygon scanners or resonant scanners.

U.S. Pat. No. 7,621,637 describes an ophthalmological apparatus for treating eye tissue, having a base station with a laser source for producing laser pulses and a scanner arranged in the base station, said scanner having movable deflection mirrors for deflecting the laser pulses in a scanning direction. The deflected laser pulses are transmitted via an optical transmission system from the base station to an application head, which covers a work region according to a scanning pattern using a mechanically moved projection optical unit. The deflection in the scanning direction, which is much faster in comparison to a mechanical movement, is superposed in the application head on the mechanical movement of the projection optical unit and consequently onto the scanning pattern thereof. A fast scanner system in the base station makes possible a fine movement of the laser pulses (microscan), which is superposed on the scanning pattern of the movable projection optical unit, which covers a large treatment region, for example the entire eye.

Such known systems make possible treatment of simple scanning patterns, for example cutting of a tissue flap, generally as a large-area piece with simple peripheral geometry. In applications in which not only areal tissue cuts in a substantially horizontally oriented treatment area are made on a common focal surface, but in which tissue volumes in the eye tissue are to be treated which extend over different focus heights and are larger than the treatment field of the focusing optical unit, the vertical movement of the projection optical unit or of a zoom system for a vertical change in the focus and thus the treatment height during treatment of the eye tissue proves to be too slow as compared to the horizontal treatment speed. Furthermore, adjacent treatment volumes result in shadowing and consequently in incomplete volume treatments.

SUMMARY

The following summary presents a simplified summary of certain features. The summary is not an extensive overview and is not intended to identify key or critical elements.

Systems, apparatuses, and methods are described for treating eye tissue using a pulsed laser beam, which does not exhibit at least some of the disadvantages of the known systems. The disclosure includes an ophthalmological apparatus for treating eye tissue using a pulsed laser beam which makes possible efficient and precise tissue volume treatment in the eye tissue.

An ophthalmological apparatus for treating eye tissue may comprise a laser source that may be configured to produce a pulsed laser beam, a scanner system that may be configured to direct the pulsed laser beam at a treatment speed in the eye tissue along a scanning treatment line, and a first scanning apparatus which is connected upstream of the scanner system and may be configured to deflect the pulsed laser beam, for producing a first additional scanning movement component, in a first scanning direction at a first scanning speed that is higher as compared to the treatment speed, such that the first additional scanning movement component is superposed on the scanning treatment line.

A ophthalmological apparatus additionally may comprise a second scanning apparatus which is connected upstream of the scanner system and may be configured to deflect the pulsed laser beam, for producing a second additional scanning movement component, in a second scanning direction, which is at an angle to the first scanning direction of the first additional scanning movement component, at a second scanning speed that is higher as compared to the first scanning speed, such that the second additional scanning movement component is superposed on the first additional scanning movement component and a scanning region is treated by the deflection of the pulsed laser beam with the first additional scanning movement component in the first scanning direction and the superposed, second additional scanning movement component in the second scanning direction, and a circuit which may be configured to control the scanner system in synchronized fashion with the first scanning apparatus and the second scanning apparatus such that the scanning region is moved by the scanner system along the scanning treatment line and tissue volume treatment is effected in the eye tissue.

The scanner system, the first scanning apparatus and the second scanning apparatus may be combined such that the scanning region, defined by the first additional scanning movement component and the second additional scanning movement component, and the treatment line extend transversely with respect to one another, and the scanning region is moved along the scanning treatment line by the scanner system for volume treatment in the eye tissue.

The scanner system may comprise a drive system which is coupled to the focusing optical unit, which focuses the laser beam into the eye tissue, and which may be configured to move the focusing optical unit in treatment directions of a treatment plane which is arranged normally with respect to the optical axis of the focusing optical unit. In such a configuration, the movement of the scanning region along the scanning treatment line by way of a movement of the focusing optical unit makes possible the performance of tissue volume treatment in the eye in a large region precisely and without shadows, for example in the entire eye region.

The scanner system may comprise a focusing apparatus may be configured to move a focus of the pulsed laser beam in the eye tissue with a directional component that extends in the projection direction in order to move the scanning region, defined by the first additional scanning movement component and the second additional scanning movement component, for volume treatment in the eye tissue with a directional component that extends in the projection direction. This configuration, including vertical movement of the scanning region, makes possible a post-shaped treatment of eye tissue.

The ophthalmological apparatus may comprise a rotation element which is connected downstream of the first scanning apparatus and the second scanning apparatus and may be configured to rotate the scanning region, defined by the first additional scanning movement component and the second additional scanning movement component, about an optical transmission axis. The circuit may be additionally configured to control the rotation element such that the rotation element rotates the scanning region about the optical transmission axis by an angle of rotation that is dependent on the scanning treatment line, such that the scanning region is moved along the scanning treatment line for tissue volume treatment in the eye tissue with a configurable orientation with respect to the scanning treatment line. By rotating the scanning region, the orientation thereof during the movement of the scanning region also can be flexibly adapted to curved, circular, spiral-shaped or spiral-arm-shaped treatment lines.

The ophthalmological apparatus may comprise a divergence modulator which may be configured to tilt the scanning region, defined by the first additional scanning movement component and the second additional scanning movement component, with respect to a reference plane. The circuit additionally may be configured to control the divergence modulator such that the divergence modulator tilts the scanning region with respect to the reference plane by a configurable tilt angle, such that the scanning region is moved along the scanning treatment line for tissue volume treatment in the eye tissue with the configurable tilt angle with respect to the reference plane. By tilting the scanning region, it is possible by movement of the tilted scanning region, to produce volume treatment without a vertical movement of the focusing apparatus or of the focusing optical unit.

The divergence modulator may comprise at least one optical element which is connected downstream of the first scanning apparatus and the second scanning apparatus and may be configured to produce, for tilting of the scanning region, a divergence of the laser beam that is dependent on the first additional scanning movement component and the second additional scanning movement component.

The optical element may be embodied to be rotatable about an optical transmission axis.

The optical element may comprise a wedge plate, a prism, a lens, a diffractive optical element and/or an aspherical mirror.

The divergence modulator may be connected upstream of the first scanning apparatus and may be configured to produce, for tilting the scanning region, a configurable divergence of the laser beam in synchronized fashion with the first scanning apparatus and/or the second scanning apparatus. The circuit additionally may be configured to control the divergence modulator such that the divergence modulator tilts the scanning region with respect to the reference plane by a tilt angle that is dependent on the scanning treatment line, such that the scanning region is moved along the scanning treatment line for tissue volume treatment in the eye tissue with a tilt, dependent on the scanning treatment line, with respect to the reference plane.

The circuit may be configured to control the scanner system such that the scanner system moves the scanning region, defined by the first additional scanning movement component and the second additional scanning movement component, along the scanning treatment line, which extends on a treatment surface within a tissue volume that is to be treated in the eye. The circuit further may be configured to control the divergence modulator such that the divergence modulator tilts the scanning region at a tilt angle that is dependent on the scanning treatment line such that, during movement of the scanning region along the scanning treatment line, a first periphery region of the scanning region is guided along an upper external surface of the tissue volume which faces a cornea surface, and a second periphery region of the scanning region, situated opposite the first periphery region, is guided along a lower external surface of the tissue volume which faces away from the corneal surface. The tilt of the scanning region, which changes with the movement on the treatment line and in which the periphery regions thereof travel external surfaces of the tissue volume to be treated, enables an efficient and flexible treatment of differently shaped tissue volumes.

The circuit may be configured to control the scanner system such that the scanning region, defined by the first additional scanning movement component and the second additional scanning movement component, is moved along the scanning treatment line, which extends in the shape of a spiral or a spiral arm within a lenticule that is to be treated in the eye.

The circuit may be configured to control the scanner system such that the scanner system moves the scanning region, defined by the first additional scanning movement component and the second additional scanning movement component, along the scanning treatment line, which extends along meridians on a treatment surface within a lenticule that is to be treated in the eye.

The circuit may be configured to control the scanner system such that the scanner system moves the scanning region, defined by the first additional scanning movement component and the second additional scanning movement component, along the scanning treatment line, which extends along a centre line within a tunnel that is to be treated in the eye.

The ophthalmological apparatus may comprise a scanning length modulator, which may be configured to change a length of the second additional scanning movement component in the second scanning direction in order to set a width of the scanning region, defined by the first additional scanning movement component and the second additional scanning movement component, and the circuit may be configured to control the scanning length modulator such that the scanning length modulator sets the width of the scanning region depending on the scanning treatment line, such that the scanning region is moved along the scanning treatment line for tissue volume treatment in the eye tissue with a width that is dependent on the scanning treatment line.

An ophthalmologic method for treating eye tissue, may comprise producing a pulsed laser beam using a laser source, directing the pulsed laser beam along a scanning treatment line using a scanner system at a treatment speed in the eye tissue, deflecting the pulsed laser beam, using a first scanning apparatus connected upstream of the scanner system, for producing a first additional scanning movement component in a first scanning direction at a first scanning speed that is higher as compared to the treatment speed, such that the first additional scanning movement component is superposed on the scanning treatment line, deflecting the pulsed laser beam, using a second scanning apparatus connected upstream of the scanner system, for producing a second additional scanning movement component, in a second scanning direction, which is at an angle to the first scanning direction of the first additional scanning movement component, at a second scanning speed that is higher as compared to the first scanning speed, such that the second additional scanning movement component is superposed on the first additional scanning movement component and a scanning region is treated by the deflection of the pulsed laser beam with the first additional scanning movement component in the first scanning direction and the superposed, second additional scanning movement component in the second scanning direction; and moving the scanning region by way of the scanner system along the scanning treatment line, such that tissue volume treatment is effected in the eye tissue, wherein the scanner system is controlled using a circuit in synchronized fashion with the first scanning apparatus and the second scanning apparatus.

BRIEF DESCRIPTION OF THE DRAWINGS

Some features are shown by way of example, and not by limitation, in the accompanying drawings. In the drawings, like numerals reference similar elements.

DETAILED DESCRIPTION

Figure 1:
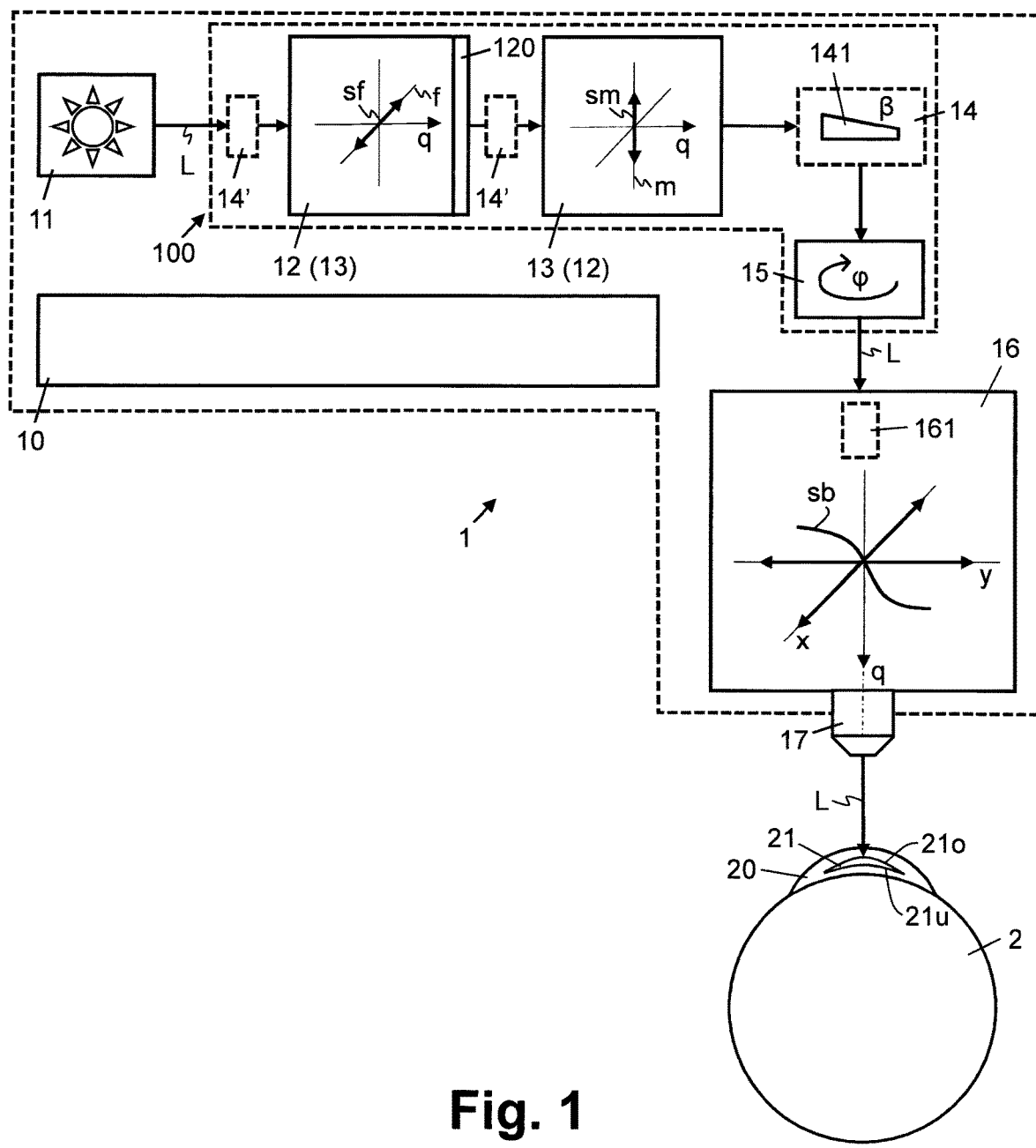
FIG. 1 shows a block diagram of an ophthalmological apparatus for treating eye tissue using a pulsed laser beam, comprising a scanner system for directing the laser beam along a scanning treatment line and two substantially faster scanning apparatuses, arranged upstream of said scanner system, for producing additional scanning movement components.

In FIG. 1, reference sign 1 refers to an ophthalmological apparatus for treating eye tissue 20 using laser pulses. Schematically illustrated in cross section is an eye 2. As is schematically illustrated in FIG. 1, the ophthalmological apparatus 1 may be configured to treat in the eye tissue 20 that is to be treated, in particular in the cornea but also in other eye tissue such as vitreous humour or lens of the eye 2, a tissue volume 21 having an upper exterior surface $21o$ and a lower exterior surface $21u$. The upper exterior surface $21o$ faces the external surface of the cornea 20 and the ophthalmological apparatus 1. The lower exterior surface $21u$ faces away from the external surface of the cornea 20 and the ophthalmological apparatus 1.

As is schematically illustrated in FIG. 1, the ophthalmological apparatus 1 may comprise a laser source 11. The laser source 11 may be configured to produce a pulsed laser beam L. The laser source 11 may be configured to produce a laser beam L with femtosecond laser pulses.

The ophthalmological apparatus 1 moreover may comprise an optical transmission system 100, a scanner system 16, and/or a focusing optical unit 17.

The focusing optical unit 17 may be configured to focus the laser beam L into the eye tissue 20. The focusing optical unit 17 may comprise one or more optical lenses. To set the focal length (focus), the focusing optical unit 17 may comprise at least one movable lens. The focusing optical unit 17 additionally may comprise one or more drives, e.g. electric motors, for automatically moving the movable lens (es) and the setting and adjustment of the focus caused thereby and the focal surface(s) that can be scanned and treated ("depth setting").

The pulsed laser beam L may be supplied to the scanner system 16 by the laser source 11 via the optical transmission system 100, which is described below. The scanner system 16 may be configured to radiate the laser beam L into the eye tissue 20 via the focusing optical unit 17 and to direct it in the eye tissue 20 in accordance with a specified x/y-scanning pattern along a scanning treatment line sb (see FIGS. 2 and 4-9). The scanner system 16 may comprise a drive system that is coupled to the focusing optical unit 17 and may be configured to move the focusing optical unit 17 in x/y-treatment directions of a treatment plane which is perpendicular with respect to the optical axis q of the focusing optical unit 17. The scanner system 16 may comprise a drive system for automatic movement of the focusing optical unit 17 in the direction of the optical axis q of the focusing optical unit 17 or of the movable lens(es) of the focusing optical unit 17, or an additional focusing apparatus 161 to direct the laser beam L in the eye tissue 20 with a directional component sz extending in the projection direction, that is to say in the direction of the optical axis q of the focusing optical unit 17, along the scanning treatment line sb, that is to say along a scanning treatment line sb with a vertical directional component (z-direction) in addition to the, or instead of the, x/y-treatment directions. The additional focusing apparatus 161 may be part of the optical transmission system 100 e.g., the additional focusing apparatus 161 may be arranged in the beam path between the laser source 11 and the focusing optical unit 17. The scanner system 16 may comprise, as an alternative or in addition to one or more drive systems, one or more beam-deflecting x/y-scanner modules, e.g. scanner modules with movable mirrors which are pivotable about one or two scan axes, or optical modulators. Arranged upstream of the focusing optical unit 17 may be a beam-deflecting scanner system having one or more movable (rotatable) mirrors.

As is schematically illustrated in FIG. 1, the optical transmission system 100 may comprise two cascaded scanning apparatuses 12, 13, which are connected upstream of the scanner system 16. In FIG. 1, the reference signs given in brackets (12), (13) are meant to signify that, in different configurations, it is either the scanning apparatus 12 that is connected upstream of the scanning apparatus 13, or the other way around. For producing additional scanning movement components sf, sm, which are superposed on the scanning treatment line sb, both scanning apparatuses 12, 13 may be configured to deflect the pulsed laser beam L in two further scanning directions f, m, which are at an angle with respect to one another, at a higher scanning speed, which may be significantly higher, as compared to the treatment speed at which the scanner system 16 that is connected downstream directs the pulsed laser beam L in the eye tissue 20 along the scanning treatment line sb. The scanning apparatus 12 may be configured to deflect the pulsed laser beam L in the scanning direction f for producing the additional scanning movement component sf at a higher scanning speed, which may be significantly higher, compared to the scanning speed at which the scanning apparatus 13 deflects the pulsed laser beam L in the scanning direction m for producing the additional scanning movement component sm, such that the additional scanning movement component sf is superposed on the additional scanning movement component sm. The scanning apparatuses 12, 13 may comprise, for example, galvano, piezo, polygon or resonant scanner modules, or AOM (acousto-optic modulator) or EOM (electro-optic modulator) scanner modules.

Figure 2:
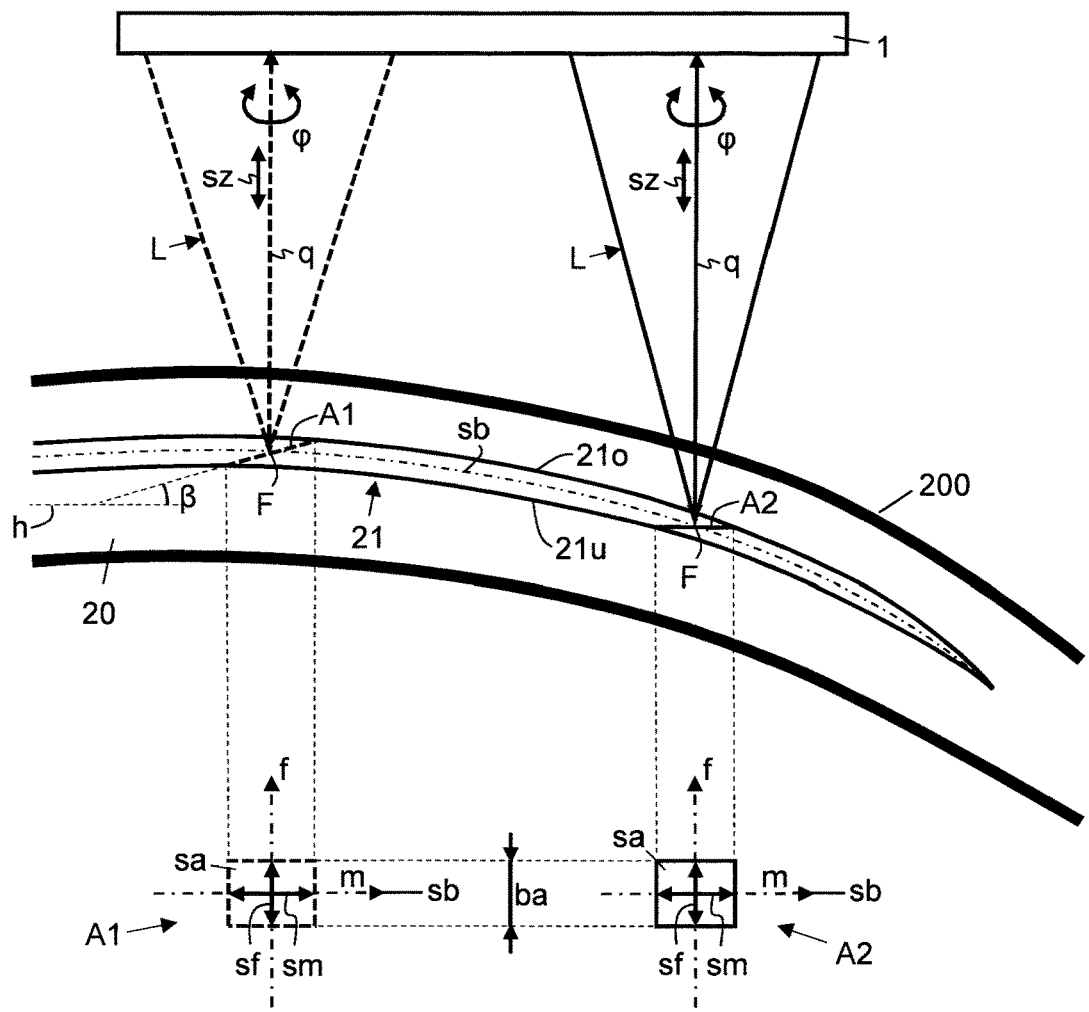
FIG. 2 shows schematically a cross section of a tissue volume that is to be treated in the eye tissue and a pulsed laser beam during the treatment of a scanning region at two different locations on a treatment line with different tilt angles, and in each case a plan view of the scanning region of interest that is defined by additional scanning movement components relative to the treatment line.

As is illustrated in FIG. 2 using the schematically illustrated plan views A1, A2, superposing the additional scanning movement component sf produced by the scanning apparatus 12 and the additional scanning movement component sm produced by the scanning apparatus 13 defines a scanning region sa which is treated by the scanning apparatuses 12, 13 with the pulsed laser beam L at higher scanning speeds, which may be significantly higher, than the treatment speed at which the scanner system 16 directs the pulsed laser beam L in the eye tissue 20 along the scanning treatment line sb.

Figure 8:
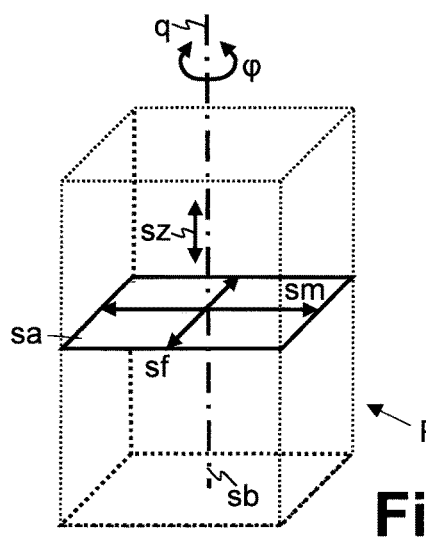
FIG. 8 shows a schematic three-dimensional view of a post-shaped tissue volume that is to be treated in the eye tissue, which is treated with a scanning region which is displaced along a treatment line that extends along the vertical centre line of the post.
Figure 9:
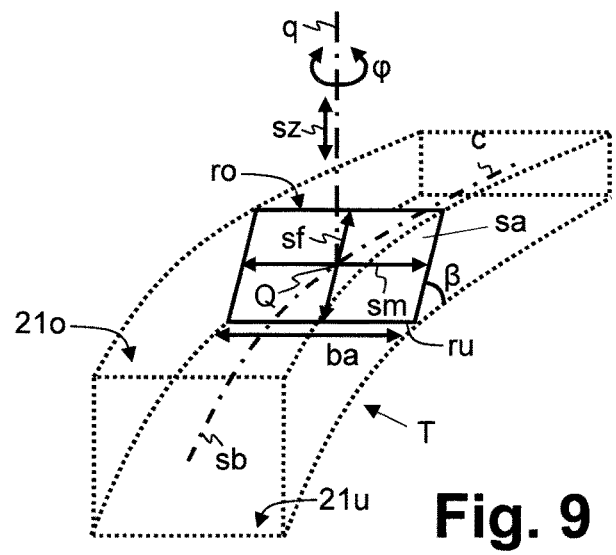
FIG. 9 shows a schematic three-dimensional view of a tunnel-shaped tissue volume that is to be treated in the eye tissue, which is treated with a scanning region that is displaced along a treatment line which extends along the centre line of the tunnel.

As is schematically illustrated in cross section in FIG. 2 and in three-dimensional illustration in FIGS. 8, 9, the scanning region sa produced by the additional scanning movement component sf, sm is moved by the scanner system 16 in the eye tissue 20 along the scanning treatment line sb, as a result of which tissue treatment in the eye tissue 20 is affected. The scanning apparatuses 12, 13 and the scanner system 16 may be configured and arranged such that their scanning directions are transverse with respect to one another and the scanning region sa produced by the additional scanning movement components sf, sm and the treatment line sb are transverse with respect to one another, such that, during the movement of the scanning region sa by the scanner system 16 along the scanning treatment line sb in the eye tissue 20, (three-dimensional) volume treatment is effected, as is illustrated for example in FIG. 8.

In the example of FIG. 8, the scanning region sa produced by the additional scanning movement components sf, sm may be moved by way of the focusing apparatus 161 and/or the focusing optical unit 17 along a treatment line sb that is normal with respect thereto, having a directional component sz extending in the projection direction, that is to say in the direction of the optical axis q of the focusing optical unit 17, e.g. to avoid shadows, from below—farther away from the outer eye or corneal surface 200, to the top—closer to the outer eye or corneal surface 200, as a result of which volume treatment in the form of a post P or a column is affected.

In the example of FIG. 9, the scanning region sa produced by the additional scanning movement components sf, sm may be tilted by a tilt angle β with respect to a reference plane relative to the treatment line sb, such that the additional scanning movement components sf, sm and the scanning region sa that is defined and produced thereby extend transversely to the treatment line sb, as is illustrated in the cross section in the example of FIG. 2. A horizontal reference plane h which extends normally with respect to the optical axis q of the focusing optical unit 17 or a reference plane extending tangentially with respect to the current working point on the treatment line sb may serve as the reference plane. The scanning region sa which is tilted relative to the treatment line sb may be moved by the scanner system 16 along the treatment line sb, as a result of which volume treatment in the form of a tunnel T is effected in the eye tissue 20.

For tilting the scanning region sa, defined by the additional scanning movement components sf, sm, the ophthalmological apparatus 1 or the optical transmission system 100 may comprise a divergence modulator 14, 14'.

As is schematically illustrated in FIG. 1, the divergence modulator 14 may comprise an optical element 141 which, incorporated in the beam path, is connected downstream of the scanning apparatuses 12, 13 and upstream of the scanner system 16. The optical element 141 may be configured to produce a divergence of the laser beam L that is dependent on the additional scanning movement components sf, sm and to thereby tilt the scanning region sa. The optical element 141 may comprise a wedge plate, a prism, a lens, a diffractive optical element and/or an aspheric mirror. The optical element 141 may be configured to be rotatable about an optical transmission axis q, as a result of which the tilting of the scanning region sa is additionally changeable and consequently configurable by a rotation about the transmission axis q. The optical element is displaced transversally with respect to the optical axis q of the focusing optical unit 17.

As is indicated in FIG. 1, the divergence modulator 14' may be incorporated in the beam path such that it is connected upstream of the scanning apparatus 12 or 13 and may be configured to dynamically change the divergence of the pulsed laser beam L supplied thereto and thereby to tilt at least one of the scanning movement components sf, sm and consequently the scanning region sa.

Figure 3:
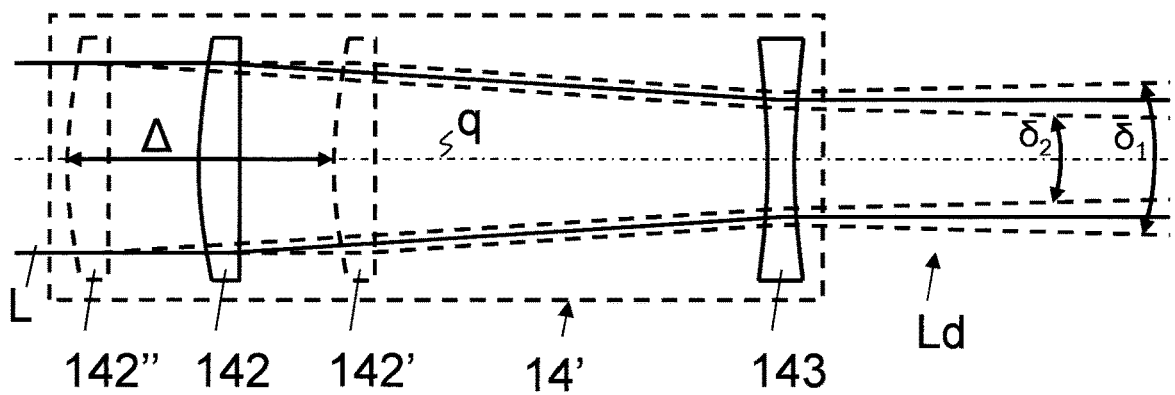
FIG. 3 shows a schematic cross section of a portion of the laser beam in a divergence modulator with at least one displaceable lens and illustrates the divergence of the laser beam which has changed due to the displacement of the lens.

FIG. 3 schematically illustrates a divergence modulator 14' having two optical lenses 142, 143 arranged in series, of which at least one is displaceable for modulating the divergence of the pulsed laser beam L on the optical transmission axis q. For the dynamic modulation of the divergence of the pulsed laser beam L, the movable lens 142 may be coupled to a movement driver. In FIG. 3, the pulsed laser beam L may have, at a first basic position 142' of the movable lens, a corresponding divergence $\delta_1$. In the case of a displacement of the movable lens 142 on the transmission axis q, the divergence of the supplied laser beam L may change continuously and have, at the position 142", which is displaced by the deflection distance Δ, a changed divergence $\delta_2$.

As is schematically illustrated in FIG. 1, the ophthalmological apparatus 1 may comprise a rotation element 15, which is connected in the beam path downstream of the scanning apparatuses 12, 13. The rotation element 15 may be configured to rotate the scanning region sa that is defined by the additional scanning movement components sf, sm by an angle of rotation φ about the optical transmission axis q, such that a scanning region sa that is rotated by the angle of rotation φ is defined, as is schematically illustrated in FIG. 9. The rotation element 15 may comprise a K-mirror or a prism for rotating the scanning region sa. The angle of rotation φ may be dynamically set and changed for example in dependence on the current position on the treatment line sb, such that the scanning region sa is oriented with a defined specified angle relative to the treatment line sb.

In FIG. 1, the reference sign 120 designates a scanning length modulator which may be configured to change a length of the additional scanning movement component sf in the scanning direction f to set a specific width ba of the scanning region sa that is defined by the additional scanning movement components sf, sm (see FIG. 2). The scanning length modulator 120 may be connected in the beam path downstream of the scanning apparatus 12 and may comprise configurable shutters, which delimit the length of the scanning movement component sf in the scanning direction f in order to achieve the desired width ba of the scanning region sa. The scanning length modulator 120 may have an electronic design and may comprise a control line from the scanning apparatus 12, via which a line scan signal of the scanning apparatus 12 is supplied to a shutter which modulates the laser beam L produced by the laser source 11 in a manner synchronized with the line scan signal such that the desired width ba of the scanning region sa is achieved. An electronic shutter also may be used to delimit peripheral regions of scanning regions sa of desired curvature and/or tilt, which without shutters go beyond a desired scanning width ba, to the desired scanning width ba. Alternatively or in addition to the scanning length modulator 120, in come configurations, a further scanning length modulator for delimiting the scanning width (and scanning height) may be provided in the scanning direction m. A two-dimensional scanning length modulator for delimiting the scanning region sa may be provided upstream of the divergence modulator 14. Such a two-dimensional scanning length modulator, e.g. in the form of a switchable mask or shutter, enables shape adaptation of the scanning region sa, e.g. a hexagonal or diamond-shaped shape adaptation or delimitation of the scanning region sa. Hexagonal delimitations, as opposed to circularly round ones, permit complete filling of volumes. Diamond-shaped scanning regions sa permit, as an alternative to non-orthogonal scanning axes or to corresponding non-orthogonal scanning movement components sf and sm, a shadow-free treatment of volumes with adjacent scanning regions sa.

As is schematically illustrated in FIG. 1, the ophthalmological apparatus 1 may comprise an electronic circuit 10 for controlling the laser source 11, the optical transmission system 100 and the modules thereof, including the scanning apparatuses 12, 13, the divergence modulator 14, 14', the rotation element 15 and the scanning length modulator 120, and also the scanner system 16, the focusing apparatus 161 and/or focusing optical unit 17 and drives of said modules, components and elements. The circuit 10 may by a programmable control apparatus and may comprise, for example, one or more processors having program and data memories and also programmed software modules for controlling the processors, and/or other programmable circuits or logic units such as ASICs (application-specific integrated circuits). For controlling the different components and modules of the ophthalmological apparatus 1, the circuit 10 may produce corresponding control signals for said components and modules.

The circuit 10 may be configured to control the ophthalmological apparatus 1 in accordance with stored treatment data such that it performs in the eye tissue 20 tissue volume treatment that is defined by said treatment data. To this end, the circuit may activate the laser source 11 and may control the scanning apparatuses 12, 13 such that they deflect the pulsed laser beam L from the laser source 11 in two scanning directions f, m which extend at an angle with respect to one another, may determine two mutually superposed scanning movement components sf, sm and thereby may define a scanning region sa, which is treated by the pulsed laser beam L. The circuit 10 additionally may control the scanner system 16 such that it moves the scanning region sa, which is defined, and treated, by the scanning movement components sf, sm, in the eye tissue 20 along a scanning treatment line sb that is defined by the treatment data and in this way effects the desired tissue volume treatment. FIGS. 1 and 2 in this respect illustrate in cross section a lenticular tissue volume 21, having a lower external surface 21*u* and an upper external surface 21*o*, which is treated in the eye tissue 20, in particular in the cornea 20.

It should be pointed out here that the term "tissue volume treatment" may comprise not only the application for tissue volume removal in the eye tissue 20 using the pulsed laser beam L, but also treatments in which the treated tissue volume 21, with correspondingly reduced energy and/or time limitation of the incident pulsed laser beam L (by control of the laser source 11), is not broken up and removed in this way, but is (therapeutically) irradiated using the pulsed laser beam L. Such therapeutically irradiated applications of the tissue volume treatment comprise the irradiation of the eye tissue of the eye lens for increasing the elasticity (e.g. by perpendicular columns parallel to the optical axis of the eye 2), the irradiation of the eye tissue of the eye lens for reversing cataracts (bleaching), the irradiation of the eye tissue of the vitreous body of the eye 2 for breaking up what are known as "floaters", the irradiation of the cornea 20 or of implants in the eye tissue for changing the refractive index or for changing the shape, the irradiation of the eye tissue of the eye lens for softening the lens in order to remove it afterwards by suction, without the use of ultrasound phaco power. Further applications of tissue volume treatment comprise perforating tissue to increase diffusion and increasing tissue strength by crosslinking using femtosecond pulses of the pulsed laser beam L.

Figure 4:
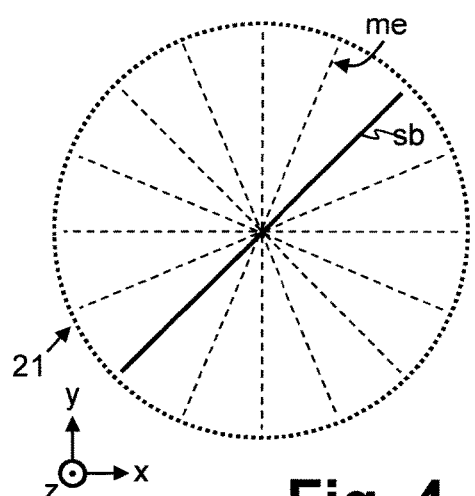
FIG. 4 shows a schematic plan view of a lenticular tissue volume, which is to be treated in the eye tissue, having a round outline, which is treated with a scanning region which is moved along a plurality of treatment lines that extend along meridians of the tissue volume.
Figure 5:
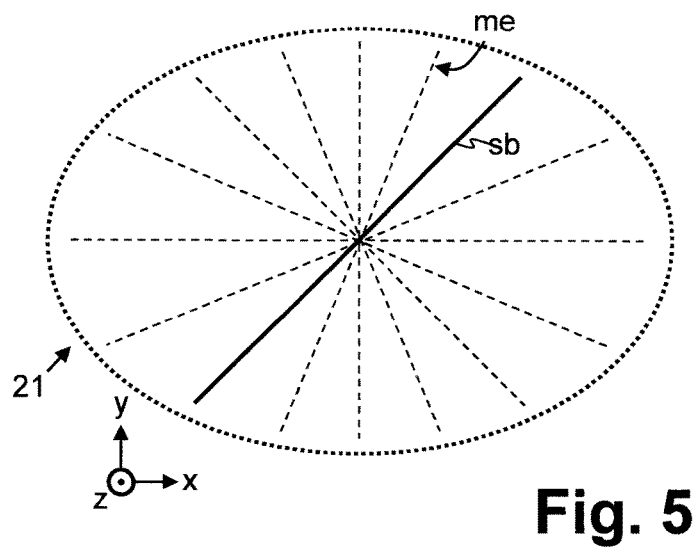
FIG. 5 shows a schematic plan view of a lenticular tissue volume that is to be treated having an elliptical outline in the eye tissue, which is treated with a scanning region that is displaced along a plurality of treatment lines which extend along meridians of the tissue volume.
Figure 6:
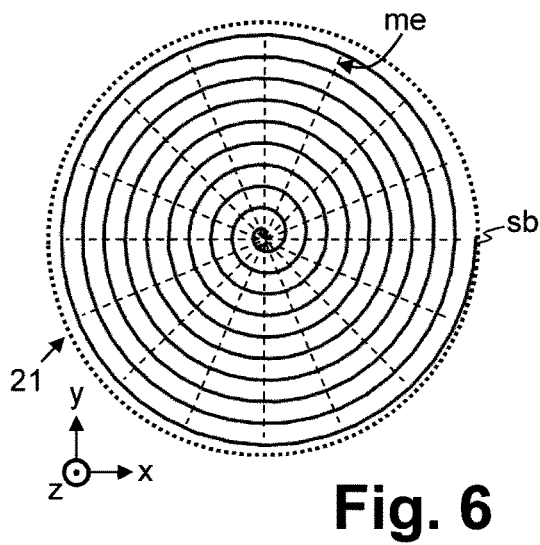
FIG. 6 shows a schematic plan view of a lenticular tissue volume that is to be treated in the eye tissue, which is treated with a scanning region that is displaced along a spiral-shaped treatment line that extends transversely to the meridians of the lenticule.
Figure 7:
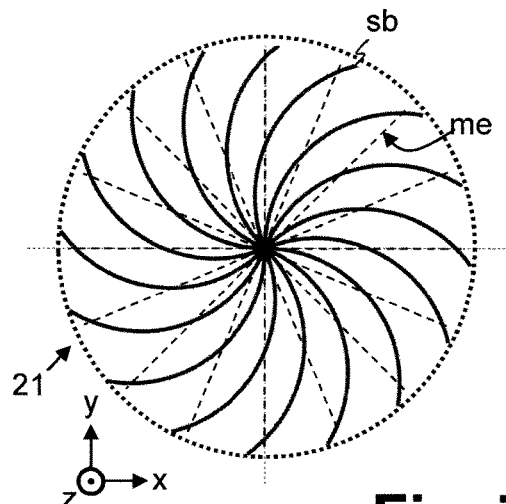
FIG. 7 shows a schematic plan view of a lenticular tissue volume that is to be treated in the eye tissue, which is treated with a scanning region that is displaced along a plurality of spiral-arm shaped treatment lines which extend transversely to meridians of the lenticule.

FIGS. 4-7 show in schematic plan view (with an optical axis of the eye 2 that extends normally with respect to the x/y-drawing plane) different variants for the treatment in the eye tissue 20 of a lenticular tissue volume 21 by moving the scanning region sa, produced by the scanning apparatuses 12, 13, along one or more treatment lines sb by way of the scanner system 16. FIG. 4 shows a section example having a plurality of treatment lines sb which extend along meridians me of a round, lenticular tissue volume 21 that is to be treated. FIG. 5 shows a section example having a plurality of treatment lines sb which extend along meridians me of an elliptical, lenticular tissue volume 21 that is to be treated. FIG. 6 shows a section example having a spiral-shaped treatment line sb, which extends transversely with respect to meridians me of a round, lenticular tissue volume 21 that is to be treated and has a spiral centre on the optical axis of the eye 2. One example of tissue volume treatment in which a tilted scanning region sa is oriented tangentially with respect to a spiral-shaped treatment line sb and is moved along said spiral-shaped treatment line sb is illustrated schematically in cross section in FIG. 10 and will be described in more detail below. FIG. 7 shows a section example having a plurality of spiral-arm-shaped treatment lines sb which, starting from the periphery of a round, lenticular tissue volume 21 that is to be treated, run towards a centre on the optical axis of the eye 2 (or vice versa) and in the process intersect the meridians me.

In addition to controlling the scanning apparatuses 12, 13 and the scanner system 16 in accordance with the treatment data for treating and moving the scanning region sa along the treatment line sb, the circuit 10 moreover may be configured to control, depending on the treatment data and the respective (current) treatment position P of the scanner system 16 on the treatment line sb, the divergence modulator 14, 14' in order to tilt the scanning region sa in a deliberate and variable manner by a tilt angle β with respect to a reference plane relative to the treatment line sb; to control the rotation element 15 in order to rotate the scanning region sa by an angle of rotation φ about the optical transmission axis q and to orient it in a targeted and variable fashion relative to the treatment line sb, for example such that the scanning region sa during the movement continues to be oriented the same relative to the spiral-shaped or spiral-arm-shaped treatment lines sb; to control the scanning length modulator 120 to set the width ba of the scanning region sa in a targeted and variable manner onto the treatment point on the treatment line sb, for example such that the scanning region sa, depending on its spatial orientation or position, is moved on the spiral-shaped treatment line sb, spiral-arm shaped treatment line sb or the treatment line sb extending along meridians with a different width sb; and/or to control the focusing apparatus 161 and/or the focusing optical unit 17 to displace the focus of the laser beam L in the projection direction.

The circuit 10 may be configured to control the ophthalmological apparatus 1 or the modules and components thereof in accordance with stored treatment data such that it treats in the eye tissue 20, by treating and moving the scanning region sa along one or more treatment lines sb (see for example the treatment lines sb in FIGS. 4-7), one or more tunnel-shaped tissue volumes T (see FIG. 9), which extend parallel to a plane that extends normally with respect to the optical axis of the eye (horizontally in a lying patient) in order to produce in a targeted fashion volume treatment in the eye tissue 20 that is defined by the treatment data (see e.g. lenticular tissue volumes in FIGS. 1 and 2). The circuit 10 may control the scanner system 16 and the focusing apparatus 161 or focusing optical unit 17 such that they travel the scanning region sa along a scanning treatment line sb, which extends along a centre line c of the tunnel T that is to be treated.

As is illustrated in FIG. 2 schematically in cross section and in FIG. 9 by way of example of the tunnel-shaped tissue volume or tunnel segment T, the circuit 10 may be configured to control, depending on the current treatment point Q of the scanner system 16 on the treatment line sb, the divergence modulator 14' such, or the divergence modulator 14 may be configured such that the scanning region sa that is treated by the scanning apparatuses 12, 13 is tilted at a tilt angle β with respect to a reference plane relative to the treatment line sb, for example to a reference plane h extending horizontally through the treatment point Q, that an upper periphery region ro of the scanning region sa is guided along the upper external surface 21o of the tissue volume 21 to be treated and a lower periphery region ru, located opposite the upper periphery region ro, of the scanning region sa is guided along the lower external surface 21o of the tissue volume 21 that is to be treated.

As is schematically shown in the plan view of FIG. 2 and as an example by way of the tunnel-shaped tissue volume or tunnel segment T of FIG. 9, the circuit 10 may be configured to control, depending on the current treatment point Q of the scanner system 16 on the treatment line sb, the scanning length modulator 120 such that the scanning region sa treated by the scanning apparatuses 12, 13 has a width ba that corresponds to the width, defined by the treatment data, of the tunnel-shaped tissue volume or tunnel segment T at the relevant treatment point Q.

As is schematically shown in cross section in FIG. 2 and as an example by way of the tunnel-shaped tissue volume or tunnel segment T of FIG. 9, the circuit 10 may be configured to control, depending on the current treatment point Q of the scanner system 16 on the treatment line sb, the rotation element 15 such that the scanning region sa treated by the scanning apparatuses 12, 13 is rotated about the optical transmission axis q by an angle of rotation φ such that the scanning region sa is oriented at a specific angle, e.g. normal, with respect to the treatment line sb.

As is schematically shown in cross section in FIG. 2 and as an example by way of the tunnel-shaped tissue volume or tunnel segment T of FIG. 9, the circuit 10 may be configured to control the focusing apparatus 161 or the focusing optical unit 17 such that the treatment line sb and consequently the treatment point Q of the scanner system 16 that is currently situated thereon and the scanning region sa which is moved along it are positioned in the eye tissue 20 at the depth in the projection direction as defined by the treatment data.

Figure 10:
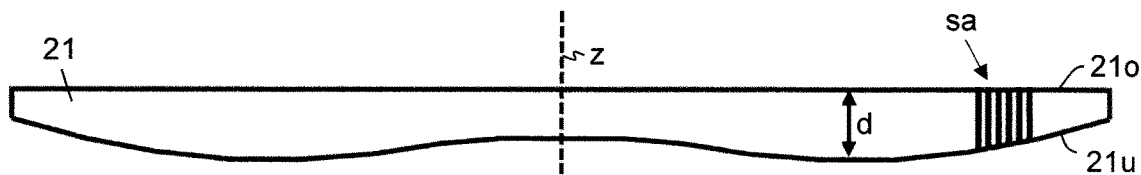
FIG. 10 shows schematically a cross section of a tissue volume in the eye tissue, which has a varying thickness and is treated using a scanning region that is displaced tangentially to a spiral-shaped treatment line along the spiral-shaped treatment line.

As is illustrated schematically in cross section in FIG. 10 by way of example by way of a round tissue volume 21 that is to be treated, which exhibits a varying thickness d, that is to say a distance between its lower external surface 21u and its upper external surface 21o which changes over the diameter of the tissue volume 21, the circuit 10 may be configured to control, depending on the treatment data and the respective (current) treatment position P of the scanner system 16 on a spiral-shaped treatment line sb (according to FIG. 6), the divergence modulator 14, 14' such that it deliberately tilts the scanning region sa such that it extends parallel to the centre axis z; to control the rotation element 15 such that it rotates the scanning region sa deliberately about the optical transmission axis q by an angle of rotation φ such that the scanning region sa is oriented at the current treatment position P tangentially with respect to the spiral-shaped treatment line sb; and to control the scanning length modulator 120 such that the scanning width (and "scanning height") of the scanning region sa in the scanning direction M is set deliberately to the thickness d, defined by the treatment data, of the tissue volume 21 at the current treatment position P.

Although examples are described above, features and/or steps of those examples may be combined, divided, omitted, rearranged, revised, and/or augmented in any desired manner. Various alterations, modifications, and improvements will readily occur to those skilled in the art. Such alterations, modifications, and improvements are intended to be part of this description, though not expressly stated herein, and are intended to be within the spirit and scope of the disclosure. Accordingly, the foregoing description is by way of example only, and is not limiting.

What is claimed is:

1. An ophthalmological apparatus for treating eye tissue, comprising:
   a laser source configured to produce a pulsed laser beam;
   a scanner system configured to direct the pulsed laser beam at a treatment speed in the eye tissue along a scanning treatment line;
   a first scanning apparatus, connected upstream of the scanner system, configured to deflect the pulsed laser beam to produce a first scanning movement component, in a first scanning direction at a first scanning speed that is higher as compared to the treatment speed, wherein the first scanning movement component is superposed on the scanning treatment line;
   a second scanning apparatus connected upstream of the scanner system, configured to deflect the pulsed laser beam to produce a second scanning movement component, in a second scanning direction, which is at an angle to the first scanning direction of the first scanning movement component, at a second scanning speed that is higher as compared to the treatment speed, wherein the second scanning movement component is superposed on the first scanning movement component, wherein a scanning region is treated by the deflection of the pulsed laser beam with the first scanning movement component in the first scanning direction and the superposed, second scanning movement component in the second scanning direction; and
   a circuit configured to control the scanner system, the first scanning apparatus, and the second scanning apparatus, wherein the scanning region is moved by the scanner system along the scanning treatment line to effect treatment of a lenticular tissue volume in the eye, wherein the treatment of the lenticular tissue volume is effected by the circuit controlling the first scanning apparatus to deflect the pulsed laser beam with the first scanning movement component in the first scanning direction, by the circuit controlling the second scanning apparatus to deflect the pulsed laser beam with the superposed, second scanning movement component in the second scanning direction, and by the circuit controlling the scanner system to direct the pulsed laser beam along the scanning treatment line, wherein the lenticular tissue volume is greater than a width of the pulsed laser beam.

2. The ophthalmological apparatus of claim 1, wherein the ophthalmological apparatus further comprises a divergence modulator configured to tilt the scanning region, defined by the first scanning movement component and the second scanning movement component, with respect to a reference plane, and the circuit is configured to control the divergence modulator such that the divergence modulator tilts the scanning region with respect to the reference plane at a configurable tilt angle, wherein, for the treatment of the lenticular tissue volume in the eye, the scanning region is moved along the scanning treatment line at the configurable tilt angle with respect to the reference plane.

3. The ophthalmological apparatus of claim 2, wherein the divergence modulator comprises an optical element configured to be rotatable about an optical transmission axis.

4. The ophthalmological apparatus according to claim 3, wherein the optical element comprises at least one of: a wedge plate, a prism, a lens, a diffractive optical element, or an aspheric mirror.

5. The ophthalmological apparatus of claim 2, wherein the divergence modulator is connected upstream of the first scanning apparatus and/or upstream of the second scanning apparatus and is configured to produce, for tilting the scanning region, synchronized with the first scanning apparatus and/or the second scanning apparatus, a configurable divergence of the pulsed laser beam, wherein the circuit is configured to control the divergence modulator such that the divergence modulator tilts the scanning region with respect to the reference plane at a tilt angle, which is dependent on the scanning treatment line, wherein, for the treatment of the lenticular tissue volume in the eye, the scanning region is moved along the scanning treatment line with a tilt, dependent on the scanning treatment line, with respect to the reference plane.

6. The ophthalmological apparatus of claim 2, wherein the circuit is configured to control the scanner system such that the scanner system moves the scanning region, defined by the first scanning movement component and the second scanning movement component, along the scanning treatment line which extends on a treatment area within the lenticular tissue volume in the eye, wherein the circuit is configured to control the divergence modulator such that the divergence modulator tilts the scanning region at a tilt angle, depending on the scanning treatment line such that, during movement of the scanning region along the scanning treatment line, a first periphery region of the scanning region is guided along an upper external surface of the corneal tissue volume which faces a corneal surface, and a second periphery region of the scanning region, situated opposite the first periphery region, is guided along a lower external surface of the corneal tissue volume which faces away from the corneal surface.

7. The ophthalmological apparatus of claim 1, wherein the scanner system comprises a focusing apparatus, configured to move a focus of the pulsed laser beam in the eye tissue with a directional component that extends in a projection direction in order to move the scanning region, defined by the first scanning movement component and the second scanning movement component, for the treatment of the lenticular tissue volume in the eye, with a directional component that extends in the projection direction.

8. The ophthalmological apparatus of claim 1, wherein the circuit is configured to control the scanner system such that the scanner system moves the scanning region, defined by the first scanning movement component and the second scanning movement component, along the scanning treatment line, which extends along meridians on a treatment area within the lenticular tissue volume that is to be treated in the eye.

9. The ophthalmological apparatus of claim 1, further comprising a rotation element, connected downstream of the first scanning apparatus and the second scanning apparatus, and configured to rotate the scanning region, defined by the first scanning movement component and the second scanning movement component, about an optical transmission axis, wherein the circuit is configured to control the rotation element such that the rotation element rotates the scanning region about the optical transmission axis by an angle of rotation that is dependent on the scanning treatment line, wherein, for the treatment of the lenticular tissue volume in the eye, the scanning region is moved along the scanning treatment line with a configurable orientation with respect to the scanning treatment line.

10. The ophthalmological apparatus of claim 1, wherein the circuit is configured to control the scanner system such that the scanner system moves the scanning region, defined by the first scanning movement component and the second scanning movement component, along the scanning treatment line, which extends in a shape of a spiral or a spiral arm within the lenticular tissue volume that is to be treated in the eye.

11. The ophthalmological apparatus of claim 1, wherein the circuit is configured to control the scanner system such that the scanner system moves the scanning region, defined by the first scanning movement component and the second scanning movement component, along the scanning treatment line, which extends along a centre line within a tunnel that is to be treated in the eye.

12. The ophthalmological apparatus of claim 1, wherein the ophthalmological apparatus further comprises a scanning length modulator, configured to change a length of the second scanning movement component in the second scanning direction in order to set a width of the scanning region, defined by the first scanning movement component and the second scanning movement component, wherein the circuit configured to control the scanning length modulator such that the scanning length modulator sets the width of the scanning region depending on the scanning treatment line, such that, for the treatment of the lenticular tissue volume in the eye, the scanning region is moved along the scanning treatment line with a width that is dependent on the scanning treatment line.

13. The ophthalmological apparatus of claim 1, wherein the scanner system is configured to direct the pulsed laser beam along a scanning treatment line in the cornea of the eye; and the circuit is configured to control the scanner system, the first scanning apparatus, and the second scanning apparatus, to move the scanning region by the scanner system along the scanning treatment line to effect the treatment of the lenticular tissue volume in the cornea of the eye.

14. A method comprising:
  directing, by a scanner system, a pulsed laser beam along a scanning treatment line in eye tissue at a treatment speed;
  deflecting the pulsed laser beam, using a first scanning apparatus connected upstream of the scanner system to produce a first scanning movement component in a first scanning direction at a first scanning speed, wherein the first scanning speed is higher as compared to the treatment speed, wherein the first scanning movement component is superposed on the scanning treatment line;
  deflecting the pulsed laser beam, using a second scanning apparatus connected upstream of the scanner system to produce a second scanning movement component, in a second scanning direction, which is at an angle to the first scanning direction of the first scanning movement component, at a second scanning speed, wherein the second scanning speed is higher as compared to the treatment speed, wherein the second scanning movement component is superposed on the first scanning movement component and a scanning region is treated by the deflection of the pulsed laser beam with the first scanning movement component in the first scanning direction and the superposed, second scanning movement component in the second scanning direction; and
  moving, by the scanner system, the scanning region along the scanning treatment line, wherein the scanner system is controlled using a circuit in synchronized fashion with the first scanning apparatus and the second scanning apparatus,
  wherein treatment of a lenticular tissue volume in the eye is effected by the deflection of the pulsed laser beam with the first scanning movement component in the first scanning direction, the deflection of the pulsed laser beam with the superposed, second scanning movement component in the second scanning direction, and direction of the pulsed laser beam along the scanning treatment line, wherein the lenticular tissue volume is greater than a width of the pulsed laser beam.

15. The method of claim 14, wherein the pulsed laser beam is directed along a scanning treatment line in the cornea of the eye; and the scanning region is moved along the scanning treatment line to effect the treatment of the lenticular tissue volume in the cornea of the eye.

16. The method of claim 14, further comprising producing, by a laser source, the pulsed laser beam.

* * * * *